United States Patent
Swoyer

(10) Patent No.: US 7,640,064 B2
(45) Date of Patent: Dec. 29, 2009

(54) SELF FIXING SPINAL CORD STIMULATION LEAD AND DELIVERY SYSTEM

(75) Inventor: John M. Swoyer, Andover, MN (US)

(73) Assignee: Greatbatch Ltd., Clarence, NY (US)

( * ) Notice: Subject to any disclaimer, the term of this patent is extended or adjusted under 35 U.S.C. 154(b) by 629 days.

(21) Appl. No.: 11/162,265

(22) Filed: Sep. 3, 2005

(65) Prior Publication Data
US 2007/0055332 A1    Mar. 8, 2007

(51) Int. Cl.
*A61N 1/05* (2006.01)

(52) U.S. Cl. ....................... 607/115; 607/119

(58) Field of Classification Search ........... 607/115, 607/116, 117, 149; 600/372, 373, 377
See application file for complete search history.

(56) References Cited

U.S. PATENT DOCUMENTS

| | | | |
|---|---|---|---|
| 4,141,365 A | 2/1979 | Fischell et al. | |
| 4,285,347 A | 8/1981 | Hess | |
| 4,374,527 A | 2/1983 | Iversen | |
| 4,419,819 A | 12/1983 | Dickhudt et al. | |
| 4,519,403 A | 5/1985 | Dickhudt | |
| 4,590,949 A | 5/1986 | Pohndorf | |
| 4,658,835 A | 4/1987 | Pohndorf | |
| 6,292,702 B1 * | 9/2001 | King et al. | 607/116 |
| 6,308,103 B1 | 10/2001 | Gielen | |
| 6,714,822 B2 | 3/2004 | King et al. | |
| 6,795,737 B2 | 9/2004 | Gielen et al. | |
| 7,319,905 B1 * | 1/2008 | Morgan et al. | 607/129 |
| 7,433,739 B1 * | 10/2008 | Salys et al. | 607/115 |
| 2004/0116977 A1 | 6/2004 | Finch et al. | |
| 2004/0243208 A1 | 12/2004 | Jordan | |

* cited by examiner

*Primary Examiner*—Carl H. Layno
*Assistant Examiner*—Jon-Eric C. Morales
(74) *Attorney, Agent, or Firm*—Michael F. Scalise

(57) ABSTRACT

Devices and methods for implanting a spinal neurological lead having at least one wing or flap extending transversely from the lead body. The wing can have a first wrapped configuration in which the wing is constrained against the lead body and a second unwrapped configuration is which the wing is unconstrained and allowed to extend outwardly. The wing can be biased to unwrap such that the wing tips change in angular position when viewed from the end, and in transverse extension when viewed from the top, but not in longitudinal position when viewed from the side. A pusher tube can be used to urge the lead from a delivery catheter, allowing the wing or wings to extend to urge a surface electrode toward the spinal cord, to maintain longitudinal position, and to be passively fixed over time. Leads according to the present invention can provide improved longitudinal stability after the lead electrode position has been properly fixed with respect to the spinal cord.

34 Claims, 7 Drawing Sheets

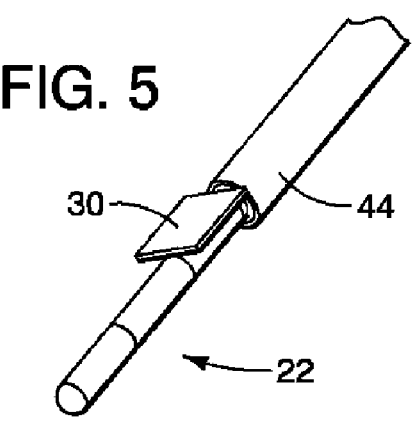
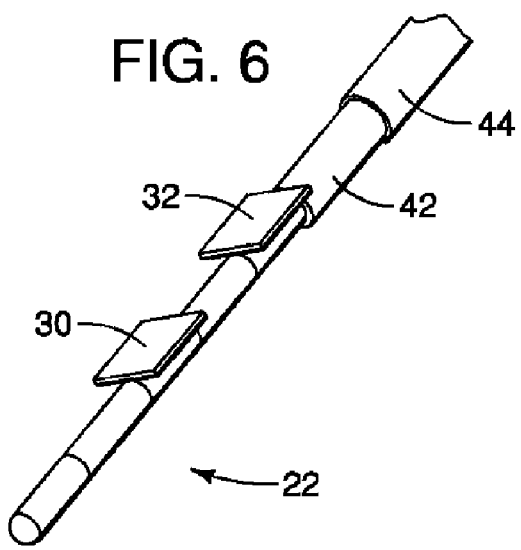
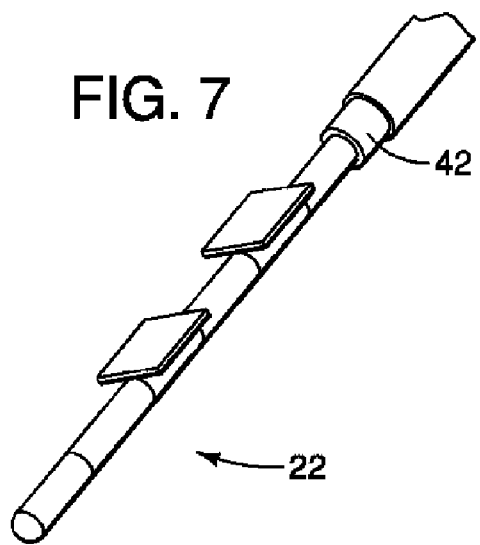

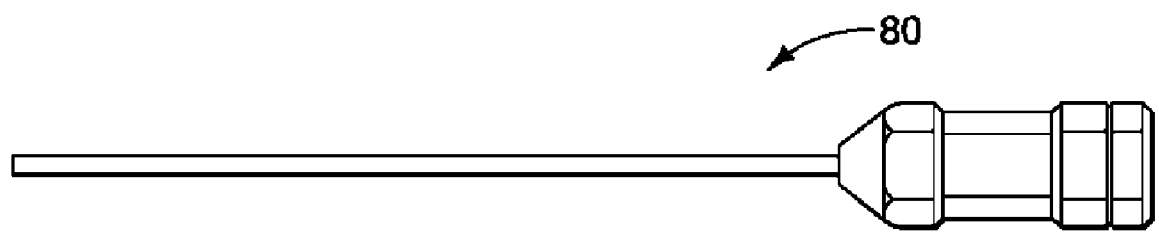
FIG. 10
FIG. 11
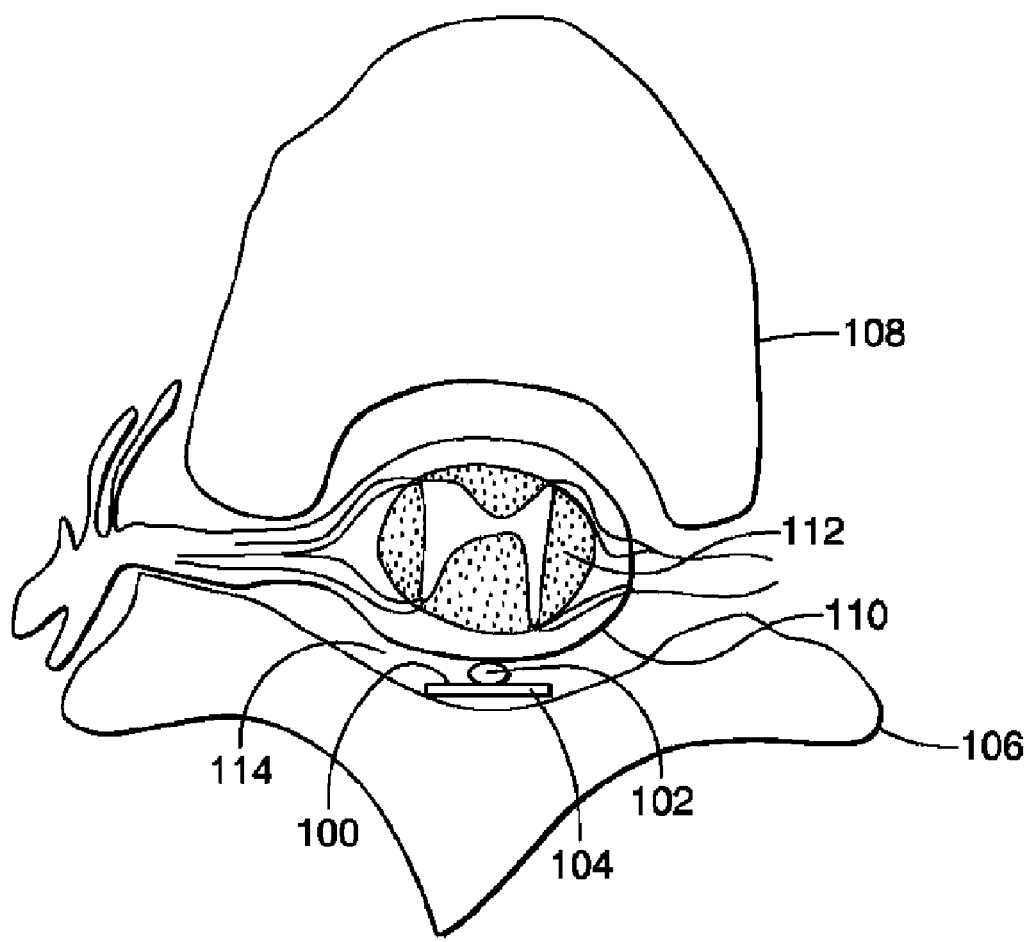

SELF FIXING SPINAL CORD STIMULATION LEAD AND DELIVERY SYSTEM

FIELD OF INVENTION

The present invention is related generally to implantable medical devices. More specifically, the present invention is related to implantable medical electrical leads.

BACKGROUND

Chronic spine pain has been dealt with recently using improved, implantable medical devices. One set of such implantable medical devices includes implantable electrical stimulation leads. Such electrical stimulation leads can be inserted through the skin, through the ligamentum flavum, and into the epidural space or epidural potential space. The lead can then be run along the spinal cord, over the dura membrane, without puncturing the dura membrane. The electrical stimulation lead can then be advanced to a particular position in the epidural space, carefully positioned over the proper location along the spinal cord. The proper location can be determined by the implanting physician using fluoroscopy and interaction with the patient.

In some procedures, with some leads, one or more of these several surface electrodes of the lead are utilized while other surface leads are not utilized. Again, the electrode selection can be determined through interaction with the patient. When the patient's pain is masked, the lead is in the proper position and the proper electrode or electrodes have been selected. This placement procedure can be rather time-consuming. With the proper surface electrodes selected and connected to the proper end connectors, the lead can be connected to an electrical signal generator and/or sensing device.

It is highly desirable that the lead, once placed, remain in place. The lead is preferably not dislodged during the remainder of the surgical procedure. Often, a suture is used to anchor an intermediate part of the lead to the body. The lead also preferably remains in place during all subsequent physical activity by the patient. Longitudinal displacement of the lead can move the surface electrodes, making them bear on a different portion of the spinal cord, no longer masking the pain. A transverse or side to side movement of the lead can have the same effect, and can also move the surface electrodes further from the spinal cord, weakening the signal, and/or requiring greater power to reach the spinal cord. Increased power consumption can decrease battery life, which may require more frequent surgical replacement of the implanted battery.

Advancing the lead through the ligamentous structures and into the epidural space can prove difficult with some patients in some procedures. Often, a stiffening member or stylet is positioned within the lead during the insertion procedure and later removed. The stylet is typically very thin, adapted to fit within a small lumen of the rather small diameter lead. This stylet may buckle during the implantation procedure. Using a stiffer member to implant the lead might prove advantageous.

What would be advantageous are methods and devices for placing the spinal stimulation lead closely along the center of the spinal cord, and also for maintaining the side to side and longitudinal position of the lead after the initial correct placement by the treating physician.

SUMMARY

The present invention provides implantable medical electrical leads, which can include an elongate lead body having a length, a proximal region, and a distal region; at least one electrical conductor disposed along the length of the lead body; and at least one electrode disposed in the lead body distal region and in electrical continuity with the conductor. At least one flap can be secured to the distal region where the flap has a first position in which the flap is disposed close to the lead body and a second position in which the flap is extended away from the lead body. In some leads, the lead body distal region has a first side and a second side disposed substantially opposite the first side. The electrode can be disposed on the first side, and the flap secured to the second side.

The flap can be biased to move from the first position to the second position when unconstrained. In some leads, the flap has a first portion extending in a first direction transversely away from a longitudinal lead body axis and a second portion extending in a second direction transversely away from the lead body longitudinal axis, in which the first and second directions are substantially opposite directions from each other. Some leads have a flap with a first portion extending on a first side of the lead central longitudinal axis and a second portion extending on a second side of the longitudinal axis opposite the first side. The flap first and second portions may lie in substantially the same plane when unconstrained in some leads. The plane does not extend through the central longitudinal axis in some embodiments.

The flap may be configured to move from the first to the second position by varying in angular position with respect to the lead longitudinal center axis when viewed from the distal end, and to vary in transverse extension from the lead longitudinal center axis when viewed from the top. However, in some embodiments, the flap movement does not substantially vary in longitudinal position when viewed from the side. The lead flap can thus be configured to move from the first to the second position without substantially changing in longitudinal position with respect to the lead and can be configured to move from the first to the second position such that a point on the wings moves substantially within a plane that is orthogonal to the lead longitudinal center axis.

The flap does not carry any electrodes in preferred embodiments, and the flap is configured to move from the first to the second position such that the flap moves away from the surface electrode.

The present invention also provides a system including the leads described above, and further includes a tubular catheter having a lumen configured to receive the lead while in the lead second position. The system may also include a pusher element adapted to be disposed along the lead body to urge the lead distally from the delivery catheter, where the pusher element may be a pusher tube adapted to be received over the lead body and within the catheter lumen. In some systems, the catheter has at least one electrically conductive distal region and an electrical conductor disposed along at least some of the catheter length and in electrical communication with the conductive distal region.

The present invention also provides methods for placing an implantable medical lead along the spinal cord. The method can include: advancing a catheter having a lumen, with the implantable medical lead disposed within the lumen into the epidural space, wherein the lead has a proximal region, a distal region, at least one electrode disposed near the distal region, and an electrical conductor extending from the proximal region to the electrode and wherein the lead has at least one wing secured to the lead body and constrained toward the lead body. The method can also include forcing the lead distal region and wing out of the catheter near the spinal cord, allowing the wing to extend away from the spinal cord and allowing the electrode to bear toward the spinal chord. The forcing may include urging a pusher element disposed along the lead body to force the lead out of the catheter.

In some methods, the pusher element is a pusher tube and the forcing includes urging the pusher tube disposed over the lead body and within the catheter lumen to force the lead out of the catheter. The forcing can include bringing the pusher tube to bear on the lead wing. Allowing the wing to extend is often substantially limited such that the wing does not change its longitudinal position with respect to the lead body during the extension. The lead wing can extend on either side of a longitudinal center axis of the lead body and on an opposite side of the longitudinal center axis from the electrode, such that the wing extending can force the lead electrode against the spinal cord and toward the spinal cord center if the lead wings are extended against surrounding tissue.

In some methods, the catheter has an electrically conductive distal region, and the methods further include urging the catheter electrically conductive region against the spinal cord and determining electrical and/or physiological properties using the electrically conductive distal portion. The determining electrical properties may include stimulating the spinal cord using the electrically conductive catheter distal region.

DESCRIPTION OF THE DRAWINGS

FIG. 5 is a fragmentary, perspective view of the lead of FIG. 4, being further pushed from the delivery catheter, allowing the most distal wing to unwrap.

FIG. 6 is a fragmentary, perspective view of the lead of FIG. 5, showing the lead further pushed from the delivery catheter, allowing the second fixation wings or flap to unwrap.

FIG. 7 is a fragmentary, perspective view of the lead of FIG. 6, showing the pusher tube and delivery catheters being proximally retracted.

FIG. 10 is a side view of a stylet that can be used to stiffen and/or push some leads into position.

FIG. 11 is a transverse, cross-sectional view through a vertebra, showing a lead according to the present invention with the fixation wing extended within the epidural space.

DETAILED DESCRIPTION

Figure 1:
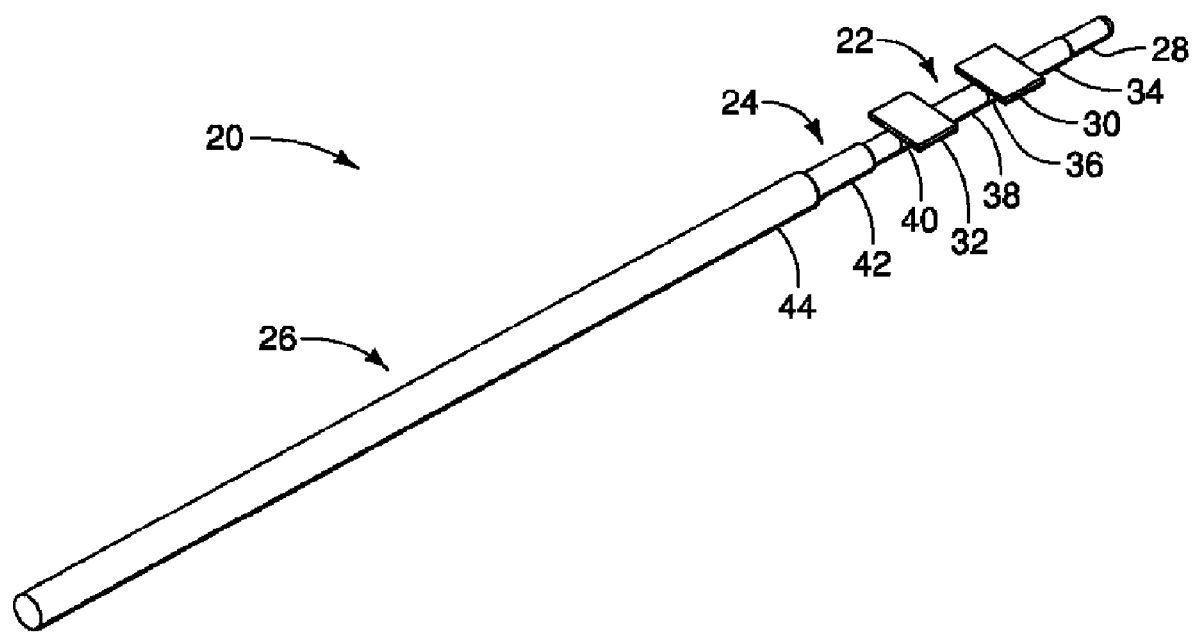
FIG. 1 is a perspective view of a system including a neurological electrical lead, a pusher tube, and a delivery catheter.

FIG. 1 illustrates a system 20 for delivering a neurological lead. System 20 includes a neurological lead 22, a pusher element or pusher tube 24, and a delivery catheter 26. Neurological lead 22 includes generally an atraumatic distal tip 28, a first electrode 34, a first fixation wing or flap 30 secured to a first lead tubular section 36, a second electrode 38, and a second fixation wing or flap 32 secured to a second lead tubular section 40. Pusher tube 24 includes a distal region 42 which may be used to push lead 22 distally. Delivery catheter 26 includes a distal region 44 which may be advanced to near the target site.

In some embodiments, the delivery catheter is between about 10 and 100 cm long and has an outer diameter of between about 0.5 mm and 5 mm. In a preferred range of embodiments, the delivery catheter is between about 20 and 80 cm long and has an outer diameter of between about 1 mm and 3.5 mm. In a more preferred range of embodiments, the delivery catheter is between about 30 and 65 cm long and has an outer diameter of between about 1.5 mm and 2.5 mm. The delivery catheter can be made of any suitable material, for example a polymeric material. Some such polymeric materials include polyamide (nylon) and polyurethane.

In some embodiments, the pusher tube is between about 12 and 110 cm long and has an outer diameter dimension to slidably fit within the delivery catheter. In a preferred range of embodiments, the pusher tube is between about 25 and 85 cm long and has an outer diameter of between about 35 and 70. The pusher tube can be made of any suitable material, for example a polymeric material. Some such polymeric materials include polyamide and polyurethane. In some embodiments, the pusher tube functionality may be replaced by a shaft, which may be made of polymeric or non-polymeric materials, for example metallic materials such a Nitinol or stainless steel. Both the delivery catheter and the pusher may be reinforced with wire braid or coils in some embodiments. Both may include a lubricious inner and/or outer surface.

In some embodiments, the lead is between about 15 and 120 cm long and has an outer diameter of between about 0.4 mm and 2.5 mm. In a preferred range of embodiments, the lead is between about 20 cm and 85 cm long and has an outer diameter of between about 0.5 mm and 2 mm. In a more preferred range of embodiments, the lead is between about 25 cm and 50 cm long and has an outer diameter of between about 0.75 mm and 1.7 mm. The lead can be made of any suitable material, for example a polymeric material. Some such polymeric materials include silicone and polyurethane.

Neurological stimulation leads are well known to those skilled in the art and are well described in numerous patents. The leads, pusher element, and delivery catheter may be made using well known techniques, including extrusion and co-extrusion.

Figure 2:
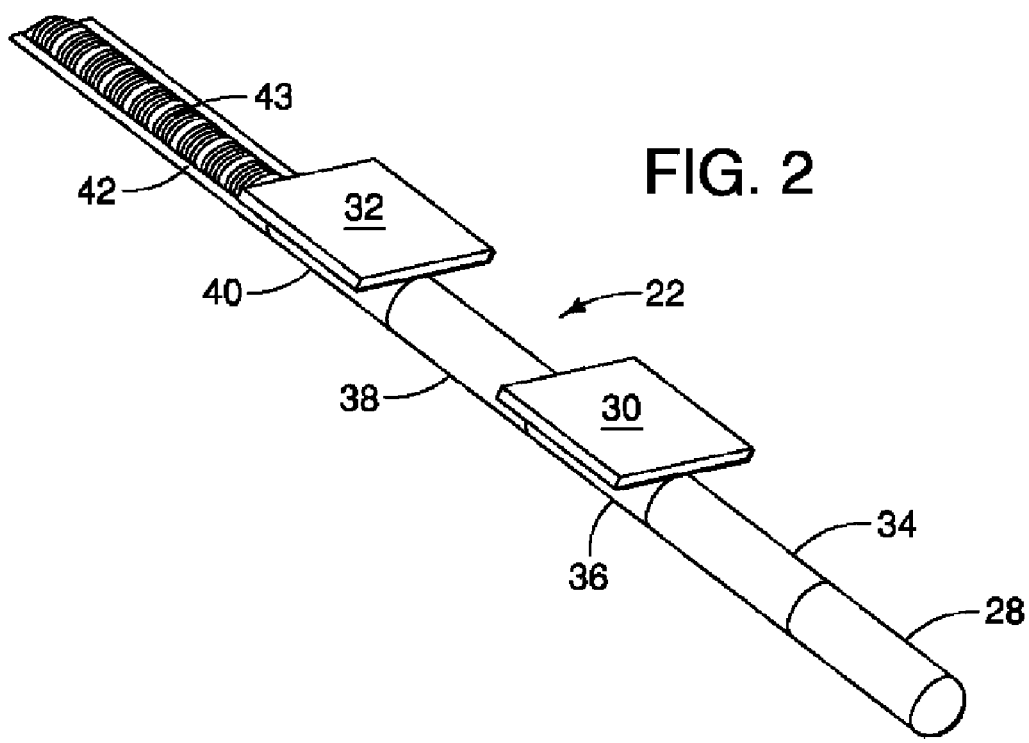
FIG. 2 is a fragmentary, perspective view of the neurological lead of FIG. 1 having fixation wings or flaps in an unwrapped or unconstrained configuration.

FIG. 2 illustrates neurological lead 22 in more detail. The previously introduced reference numerals are as previously described with respect to FIG. 1. Wings or flaps 30 and 32 are in an extended, unwrapped or unconstrained configuration. Electrodes 34 and 38 are illustrated as surface electrodes which extend circumferentially around the entire lead body. In some embodiments, the electrodes are surface electrodes which extend only partially around the lead body, on the opposite side of the lead body from wings 30 and 32. A coil 43 may be seen, disposed within the lead body, for delivering and/or receiving the electrical signals. The coil may be formed of a multi-conductor coil or any other suitable conductor, well-known to those skilled in the art. Electrodes 34 and 38 may be used to sense electrical signals and/or stimulate the body with electrical stimulation signals.

In the embodiment illustrated in FIG. 2, fixation wings or flaps 30 and 32 are secured to electrically insulating tubular sections 36 and 40. In other embodiments, wings 30 and 32 may be secured directly opposite the surface electrodes disposed on the opposite side of the lead body. The unfurled or unwrapped wings or flaps may be used to more accurately and consistently position the surface electrodes, allowing the electrodes to be disposed only on the underside of the lead body, providing for more directed electrical stimulation with less power usage and longer resulting battery life. In some embodiments, the fixation wings may have an unconstrained positioned that arcs away from the lead body below (FIG. 9A). In still other embodiments, the unconstrained positioned of the wings may be slightly arced toward the lead body (FIG. 9B), not extending into a full plane as illustrated in FIG. 2.

Figure 3:
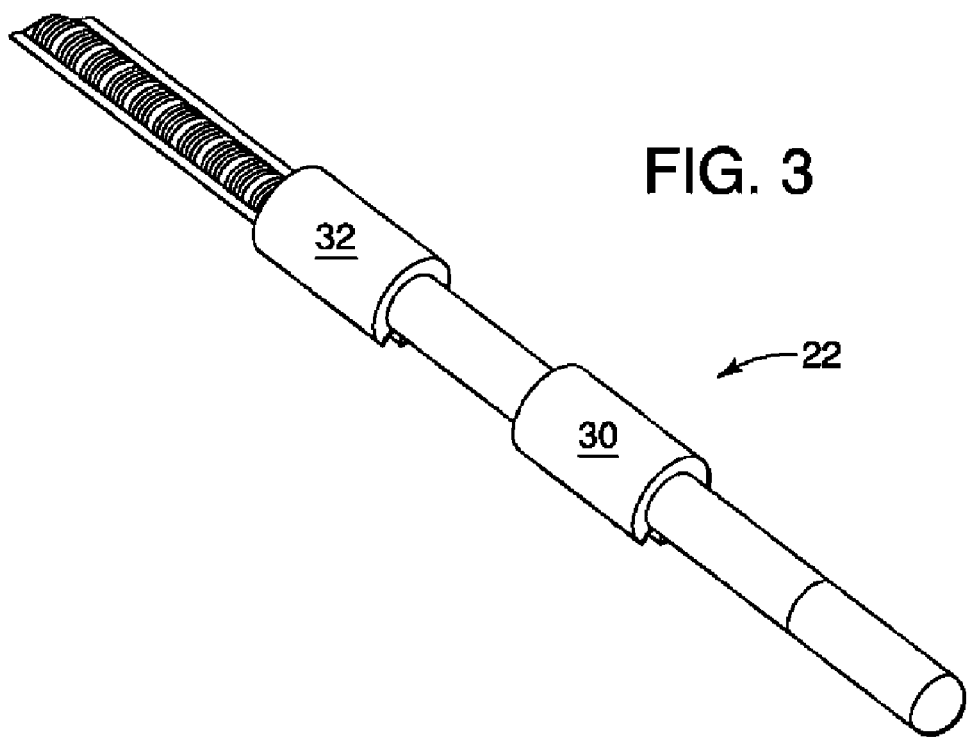
FIG. 3 is a fragmentary, perspective view of the lead of FIG. 2, with the fixation wings or flaps shown in a constrained or wrapped configuration.

FIG. 3 illustrates lead 22, having fixation wings 30 and 32 shown in a wrapped, curled, or constrained positioned closer about the lead body. In some embodiments, the wing tips may overlap each other in the wrapped configuration. In a preferred embodiment, the wing tips do not overlap each other, but may closely approach each other in the wrapped configuration. With the wings in the wrapped configuration, the wings and lead body may be retracted proximally into the delivery catheter.

Figure 4:
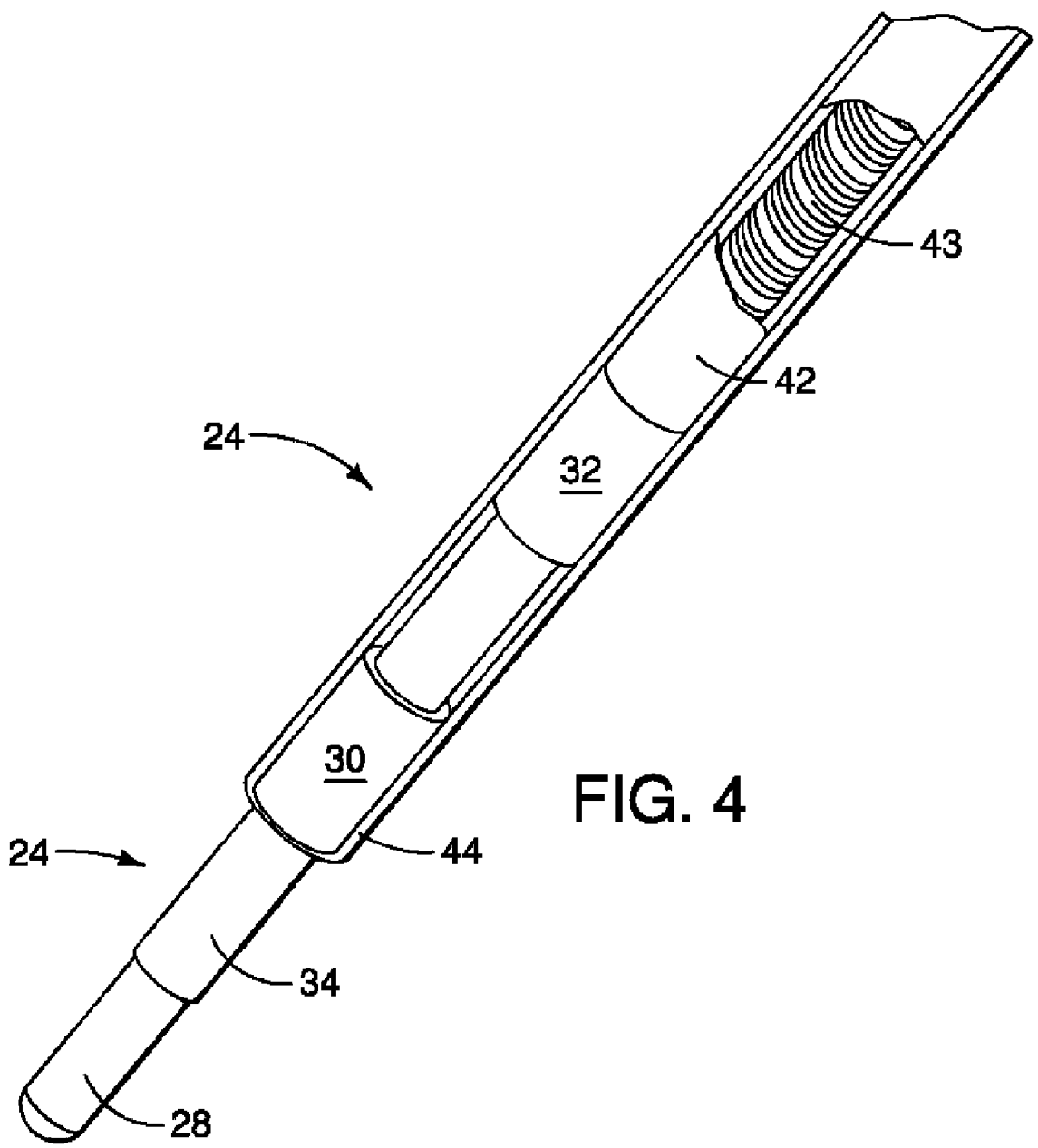
FIG. 4 is a fragmentary, perspective, cut-away view of the system of FIG. 1, having the lead partially extended from the delivery catheter, being pushed by the pusher tube.

FIG. 4 illustrates lead 22 retracted at least partially proximally into delivery catheter 24. Wings 30 and 32 may be seen constrained within the outer delivery catheter 24. Pusher tube distal region 42 may be seen butting against the proximal fixation wings 32. In some embodiments, a pusher element, such as a wire or a shaft may be used to push out the lead. Lead 22 may be further proximally retracted into delivery catheter 24, and the system prepared for lead implantation.

The delivery catheter may be advanced to the implantation site using methods well-known to those skilled in the art. The delivery catheter body may be advanced through an introducer or needle, into the epidural space. The delivery catheter may be pushed along the spine, until the catheter distal region is near the target site. The delivery catheter may be formed of rather stiff, pushable material, having greater kink resistance than a neurological catheter having a thin stylet within. The delivery catheter may thus be forced through the epidural space and tissue with less concern for kinking or bending of the neurological lead, which may be protected by the outer catheter during at least part of the delivery process. When the delivery catheter distal region is near the target site, the neurological lead can be deployed distally from the delivery catheter, either by pushing the pusher catheter further distally or maintaining the position of the pusher tube while retracting the outer delivery catheter.

In some embodiments, the final placement of the lead is preceded or accompanied by mapping using a mapping electrode or device having similar functionality. In some methods, a separate mapping lead is used to determine the optimal position for a stimulation or sensing lead placement. In other methods, the delivery catheter itself carries external or surface electrodes which may be used to map the optimal location. In still other methods, the delivery catheter is suitably transparent to the electrical stimulation signals from the lead within, for example, though holes suitably placed through the delivery catheter wall. Mapping may also be performed by partially advancing the stimulation lead and using the exposed electrodes.

In some methods, the final placement of the lead is preceded by mapping using the lead electrode for the mapping. In one such method, the distal most lead electrode is forced from the delivery catheter and used to perform the mapping, for example, test stimulation. After proper placement, the delivery catheter can be removed to expose any remaining electrodes and flaps or wings.

FIG. 5 illustrates lead 22 being urged from within distal region 44 of delivery catheter 26. First wing or flap 30 may be seen as released, unfurled, or unconstrained from delivery catheter 26.

FIG. 6 illustrates lead 22 further urged from delivery catheter distal region 44. First wing 30 and second wing 32 are now both deployed and pushed from delivery catheter distal region 44 by pusher tube distal region 42.

FIG. 7 illustrates both pusher tube distal region 42 and delivery catheter distal region 44 being proximally retracted from about lead 22.

Figure 8:
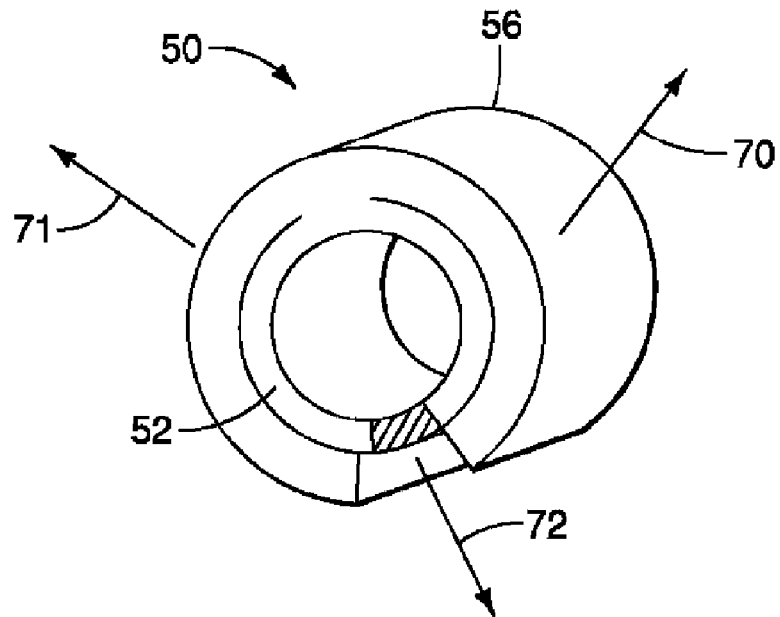
FIG. 8 is a perspective view of one lead body section having the wings or flap wrapped or curled about the lead body.

FIG. 8 illustrates a lead body section 50 with a tubular portion 52, and a wing 56 in the constrained, wrapped configuration. Directional arrows 70 and 71 indicate the direction of the unfurling of wing 56 and the general direction of the force applied by the two wing portions against the surrounding tissue. Directional arrow 72 indicates the resultant movement of lead body section 52, which results from the urging of the wing portions against the surrounding tissue, which can act to force the lead body and surface electrode against the dura, in the direction of the spinal cord. Lead body section 50 also includes a lumen within, which can extend over part or most of its length. The lumen can receive a removable stiffening member such as a stylet within. The stylet can be used to stiffen and/or to push the lead from the delivery catheter, either alone or in conjunction with a pusher tube. Some lead bodies have no lumen within and is used with a pusher tube without a stylet.

Figure 9:
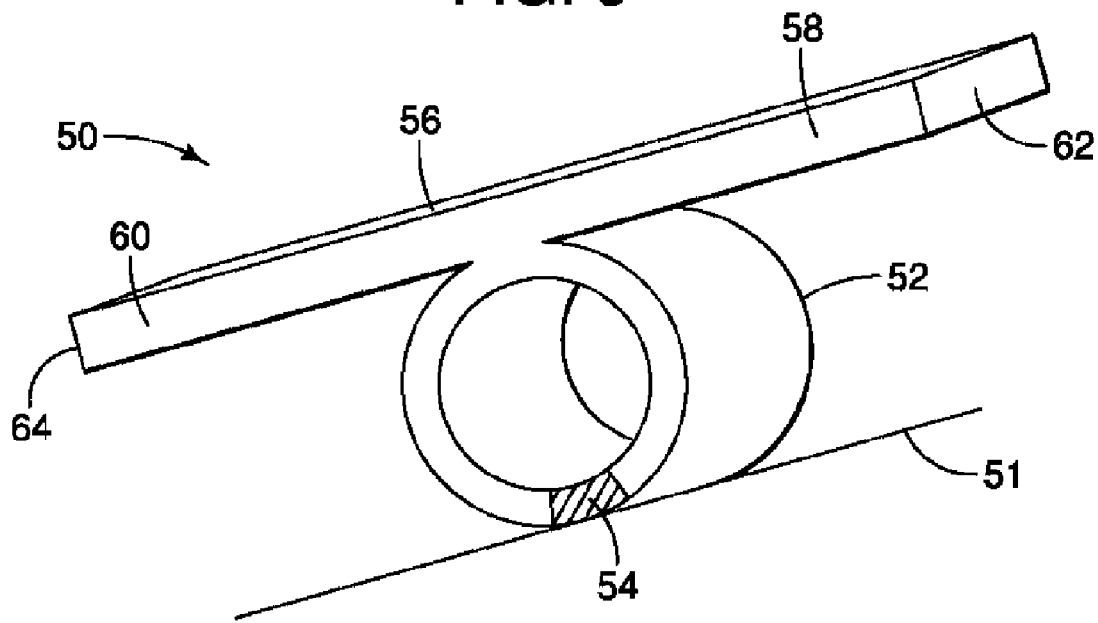
FIG. 9 is a perspective view of the lead body section of FIG. 8, showing the fixation wings or flap in an unconstrained configuration.
Figure 9A:
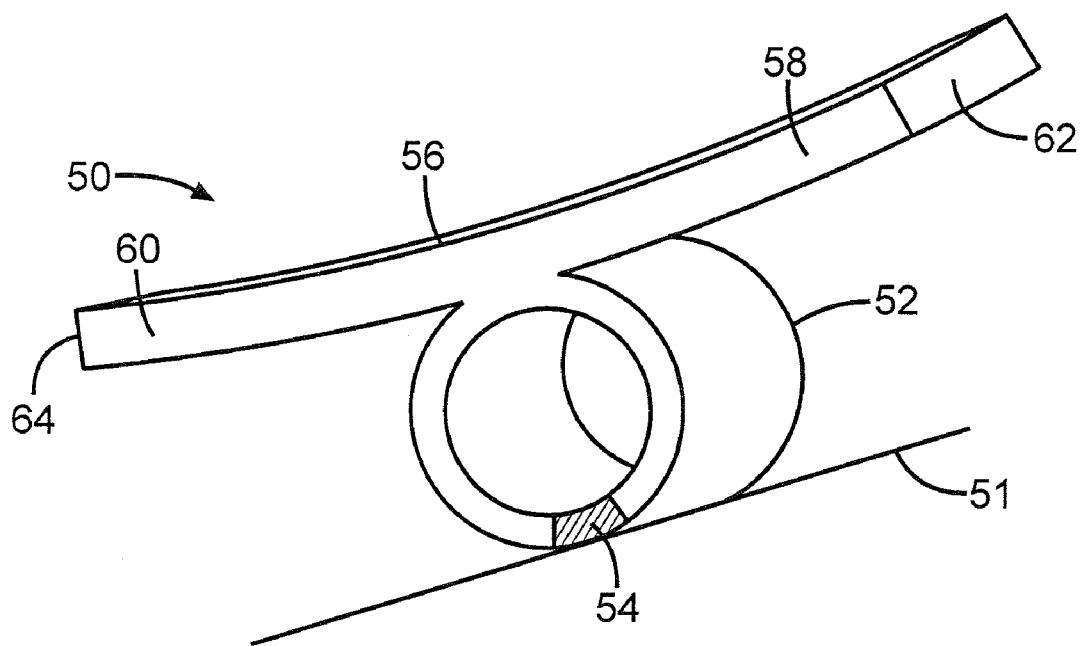
FIG. 9A is a perspective view of the lead body section of FIG. 8, showing the fixation wings or flap in an unconstrained configuration arced away from the lead body.
Figure 9B:
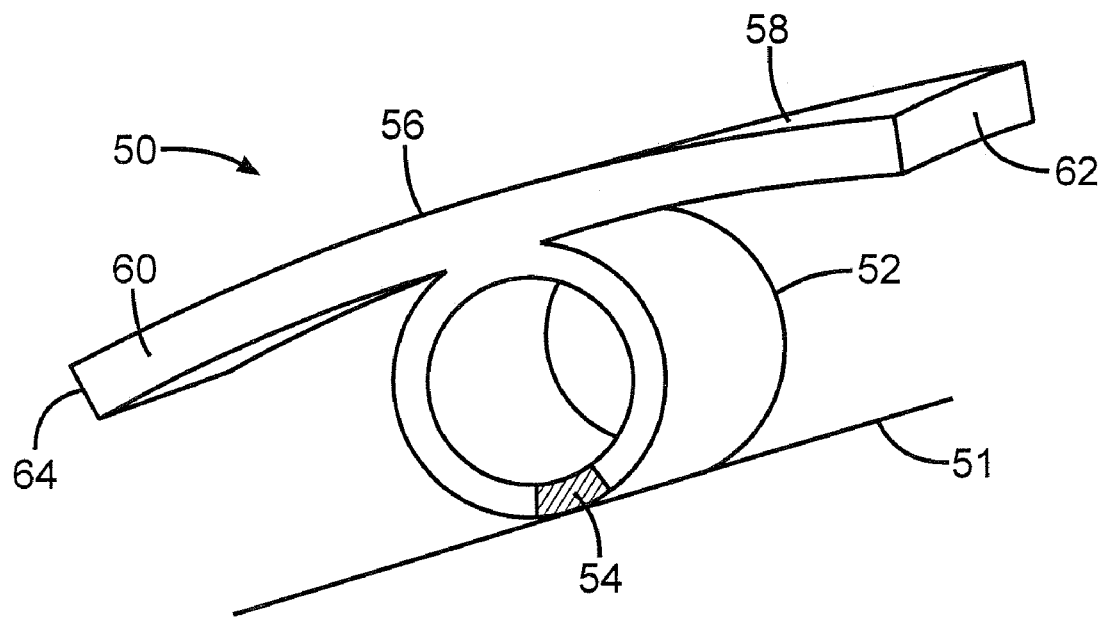
FIG. 9B is a perspective view of the lead body section of FIG. 8, showing the fixation wings or flap in an unconstrained configuration arced toward the lead body.

FIG. 9 illustrates lead section 50 in the unwrapped or unconstrained configuration. Wing 56 may be seen to have two portions, 60 and 58. Wing tips 62 and 64 may also be seen. A surface electrode 54 may be seen disposed on the surface of lead body tubular region 52, forced against highly diagrammatic dura matter 51. Surface electrode 54 covers only a portion of tubular section 52, which can allow for reduced power consumption in the electrical stimulation unit and battery. Wing 56 can thus act to force surface electrode 54 against dura matter 51, closer to the spinal cord.

FIG. 10 illustrates a stylet 80 that can be used with some leads.

FIGS. 8 and 9 show that the wing is circumferentially disposed about the lead body in the wrapped or constrained configuration. Wing tips 62 and 64 may be seen to move away from lead body 52, but not to move longitudinally with respect to lead body 52. This means that the wing unwrapping does not urge the lead body to move longitudinally. This also means that the wing unwrapping does not act to dislodge the lead from the previous position.

A plane or several planes may be viewed as passing through the lead body and being transversely or orthogonally disposed with respect to the longitudinal central axis of the lead body. At least one plane may be viewed as passing through the lead body in the region of fixation of the wing to the tubular lead body. Such a plane describes a path over the surface of the wing while in the wrapped or constrained configuration. When the wing is unwrapped or released, the same plane may describe the same surface line on the wing in many embodiments of the present invention, as the wing has not moved longitudinally with respect to the lead body.

Releasing the wrapped wing portions may thus act to urge the portion of the lead body opposite the wing attachment region in a direction opposite to the wing attachment region, when the wings are disposed within tissue or a viscous environment. This may be contrasted with wing portions wrapped or constrained longitudinally along the lead body longitudinal axis, where the wing tips move longitudinally with respect to the lead body once released. Such a longitudinal wing tip movement would act to move the lead body longitudinally when the wings are disposed within tissue or a viscous environment.

In some methods according to the present invention, the lead placement is tested after the wings are deployed, with the lead body moved longitudinally after deployment, to further adjust the lead position. This adjustment may be based on testing using the lead surface electrodes in some methods. Selection of which electrodes to connect may be done at this time in some methods.

FIG. 11 illustrates a winged lead 100 having a body 102 and wing 104 disposed within an epidural space 114, with lead body 102 urged against dura matter 110. Lead body 102 is just urged close to spinal cord 112. Spinal cord 112 may be seen disposed between vertebral body portions 106 and 108.

FIG. 11 shows that the winged lead 100 can have two advantages. The correct orientation of the surface electrode may be maintained as the rotation of the lead about its center is inhibited by the wings. This may allow the use of a surface electrode disposed over only a portion of the lead body, in a direction toward the spinal cord. The movement of the surface electrode and lead away from the spinal cord may also be inhibited by the wings. In FIG. 11, this means that the up and down movement of the lead body is inhibited by the wings. Additionally, the longitudinal movement of the lead along the spinal cord is inhibited by the wings, both during the implantation process, and long afterwards. The lead wings may be passively fixed over time by the body. This can provide improved resistance to lead displacement during physical exertion by the patient.

Some aspects of some examples and embodiments of the present invention have been discussed in the specification. The scope of the invention is given in the claims which follow.

What is claimed is:

1. A system including an implantable medical electrical lead comprising:
   a) an elongate lead body having a length extending from a proximal region to a distal region, wherein at least the distal region has a longitudinal center axis;
   b) at least one electrical conductor disposed along the length of the lead body;
   c) at least one electrode disposed in the lead body distal region and in electrical continuity with the at least one conductor; and
   d) at least two fixation flaps not carrying an electrode and supported opposite each other substantially at a tangential location with respect to a periphery of a sidewall of the distal lead region, wherein the tangential location of the fixation flaps is spaced from the longitudinal center axis of the lead body directly opposite the electrode, and wherein when the at least two fixation flaps are in a first position they are constrained close to the lead body, the at least two fixation flaps in the constrained position, do not cover the at least one electrode, and wherein when the at least two fixation flaps are in a second position, they extend away from the lead body and away from each other for urging the electrode toward body tissue.

2. The lead of claim 1 wherein the lead body distal region has a first side and a second side disposed substantially opposite the first side, and wherein the at least one electrode is disposed on the first side with the at least two fixation flaps being secured to the distal region second side.

3. The lead of claim 1 wherein the at least two fixation flaps are supported on opposite sides of an intermediate portion attached to the lead body at the tangential location between the two flaps.

4. The lead of claim 3 wherein each of the at least two fixation flaps have opposing edges on opposite sides of the lead body and wherein the opposing edges are configured to move away from each other when the at least two fixation flaps move from the first position to the second position.

5. The lead of claim 1 wherein the at least two fixation flaps are biased to move from the first position to the second position when unconstrained.

6. The lead of claim 1 wherein the at least two fixation flaps lie in substantially one plane when unconstrained.

7. The lead of claim 1 wherein the at least two fixation flaps are configured to move from the first to the second position by varying in angular position with respect to the lead longitudinal center axis when viewed from the distal end, and to vary in extension distance from the lead longitudinal center axis when viewed from the top, but to not substantially vary in longitudinal position when viewed from the side.

8. The lead of claim 1 wherein the at least two fixation flaps are configured to move from the first to the second position without substantially changing in longitudinal position with respect to the lead and wherein the at least two fixation flaps are wrapped in opposite winding directions relative to each other when in the first position.

9. The lead of claim 1 wherein each of the at least two fixation flaps is configured to move from the first to the second position such that a point on least one of the flap portions moves substantially within a plane that is orthogonal to the lead longitudinal center axis.

10. The lead of claim 1 wherein the at least two fixation flaps are configured to move from the first to the second position such that each of them moves away from a surface of the electrode.

11. The lead of claim 1 wherein each of the fixation flaps is configured to move from the first to the second position such that the fixation flap splays away from the electrode further than the furthest point of the lead body lying in the same transverse plane that includes both the electrode and the furthest point of the lead body.

12. The system of claim 1 further comprising a tubular catheter having a lumen configured to receive the lead while in the lead second position.

13. The system of claim 12 further comprising a pusher element adapted to be disposed along the catheter to urge the lead distally from the delivery catheter.

14. The system of claim 13 wherein the pusher element is a pusher tube adapted to be received over the lead body and within the catheter lumen.

15. The system of claim 12 wherein the catheter has at least one electrically conductive distal region and an electrical conductor disposed along at least some of the catheter length and in electrical communication with the conductive distal region.

16. The system of claim 12 wherein the lead body has a lumen within for at least part of its length, and further comprising a stylet configured to be received within the lead body lumen.

17. The system of claim 16 further comprising a pusher element adapted to be disposed along the lead body to urge the lead distally from the delivery catheter.

18. The lead of claim 1 wherein the at least two fixation flaps arc away from the longitudinal center axis of the lead when unconstrained.

19. The lead of claim 1 wherein the at least two fixation flaps arc towards the longitudinal center axis of the lead when unconstrained.

20. A method for placing an implantable medical lead along a body tissue, the method comprising:
   a) advancing a catheter having a lumen into the epidural space with the implantable medical lead disposed within the lumen, wherein the lead has a proximal region, a distal region having a longitudinal center axis, at least one electrode disposed near the distal region, and an electrical conductor extending from the proximal region to the electrode, and wherein the lead has at least two fixation flaps not carrying an electrode and supported opposite each other at a tangential location with respect to a periphery of a sidewall of the distal lead region, wherein the tangential location of the fixation flaps is spaced from the longitudinal center axis directly opposite the electrode and wherein when the lead distal region is housed inside the catheter, the at least two fixation flaps are constrained toward the lead body, the at least two fixation flaps not covering the at least one electrode when they are constrained toward the lead body; and
   b) forcing the lead distal region out of the catheter, and into the body tissue with the at least two fixation flaps moving into an unconstrained position extending away from the lead body to thereby help the electrode bear against the body tissue.

21. The method of claim 20 including urging a pusher element disposed along the lead body to force the lead out of the catheter.

22. The method of claim 21 wherein the pusher element is a pusher tube and the forcing includes urging the pusher tube disposed over the lead body and within the catheter lumen to force the lead out of the catheter.

23. The method of claim 22 wherein the lead body includes a removable stylet disposed within during at least some of the forcing.

24. The method of claim 21 wherein the pusher element is a removable stylet disposed within the lead body during at least some of the forcing.

25. The method of claim 21 wherein the forcing includes bringing the pusher tube to bear on the at least two fixation flaps.

26. The method of claim 20 including the step of allowing the at least two fixation flaps to extend is substantially limited to extending such that the flaps not change their longitudinal positions with respect to the lead body during the extension.

27. The method of claim 20 wherein the at least two fixation flaps lie in substantially the same plane when unconstrained.

28. The method of claim 20 including providing the at least two fixation flaps being disposed on an opposite side of the lead body from the electrode with the flaps opening urging the electrode in a direction away from the flaps.

29. The method of claim 20 including providing the catheter having an electrically conductive distal region, and further comprising urging the catheter electrically conductive region near a spinal cord and determining at least one of electrical or physiological properties using the electrically conductive distal portion.

30. The method of claim 29 wherein determining electrical properties includes stimulating the spinal cord using the electrically conductive catheter distal region.

31. The method of 20 further comprising urging the lead body partially out of the catheter to dispose the electrode near the body tissue and determining at least one of electrical or physiological properties using the electrode, followed by completely urging the lead body out of the catheter.

32. The method of claim 20 including the at least two fixation flaps arcing away from the longitudinal center axis of the lead when they are in the unconstrained position.

33. The method of claim 20 including the at least two fixation flaps arcing towards the longitudinal center axis of the lead when they are in the unconstrained position.

34. An implantable medical electrical lead, which comprises:
   a) an elongate lead body having a length extending from a proximal region to a distal region, wherein at least the distal region has a longitudinal center axis;
   b) at least one electrical conductor disposed along the length of the body;
   c) at least one electrode disposed in the lead body distal region an in electrical continuity with the at least one conductor; and
   d) at least two fixation flaps not carrying an electrode and supported opposite each other at a tangential location with respect to a periphery of a sidewall of the distal lead region, wherein the tangential location of the fixation flaps is spaced from the longitudinal center axis directly opposite the electrode, and wherein when the at least two fixation flaps are in a constrained position, they are disposed close to the lead body, the at least two fixation flaps do not cover the at least one electrode when in a constrained position and wherein when the at least two fixation flaps are in an unconstrained position, they arc away from the longitudinal center axis of the lead body and away from each other for urging the electrode toward body tissue.

* * * * *

UNITED STATES PATENT AND TRADEMARK OFFICE
CERTIFICATE OF CORRECTION

PATENT NO. : 7,640,064 B2
APPLICATION NO. : 11/162265
DATED : December 29, 2009
INVENTOR(S) : John M. Swoyer It is certified that error appears in the above-identified patent and that said Letters Patent is hereby corrected as shown below:

Column 7, Claim 1, line 51 - delete "substantially"

Column 8, Claim 9, line 31 - delete "least one of"

Column 10, Claim 34, line 34 - "an" should be "and"

Signed and Sealed this

Eighth Day of June, 2010

David J. Kappos
*Director of the United States Patent and Trademark Office*